United States Patent [19]

Schwebel et al.

[11] 4,089,334
[45] May 16, 1978

[54] PYROTECHNICALLY POWERED NEEDLELESS INJECTOR

[76] Inventors: Paul R. Schwebel, 617 Hampshire Rd., Westlake, Calif. 91361; Manuel N. Friend, 519 Roselawn Ave., Turlock, Calif. 95380

[21] Appl. No.: 730,421

[22] Filed: Oct. 7, 1976

[51] Int. Cl.$^2$ .............................................. A61M 5/30
[52] U.S. Cl. ................... 128/173 H; 128/215; 128/218 A
[58] Field of Search .......... 128/173 H, 173 R, 215 R, 128/218 A, DIG. 11, 216 R, 218 PA, 218 G, 218 C

[56] References Cited
U.S. PATENT DOCUMENTS

| | | | |
|---|---|---|---|
| 2,322,245 | 6/1943 | Lockhart | 128/173 H |
| 2,762,369 | 9/1956 | Venditty | 128/173 H |
| 2,762,370 | 9/1956 | Venditty | 128/173 H |
| 3,841,328 | 10/1974 | Jensen | 128/218 A |

FOREIGN PATENT DOCUMENTS 692,735   8/1964   Canada .............................. 128/173 H

*Primary Examiner*—Robert W. Michell
*Assistant Examiner*—Henry J. Recla

[57] ABSTRACT

A pyrotechnically powered needleless injector for introducing predetermined quantities of medicaments interstitially through the skin. The injector includes a barrel formed to receive an ampul. An elongated disposable ampul, containing a quantity of a selected medicament and having an orifice at one end, a deflagatory gas-generating pyrotechnic charge at its other end, and a gas operated piston positioned between the charge and the medicament to eject the medicament through the orifice under high pressure upon detonation of the charge, is adapted to be inserted into and releasably secured in the barrel. The barrel is rotatably and slidably mounted to a housing containing a firing mechanism which is armed by relative motion of the barrel and housing. A triggering mechanism in the housing activates the firing mechanism to detonate the charge within the ampul.

8 Claims, 11 Drawing Figures

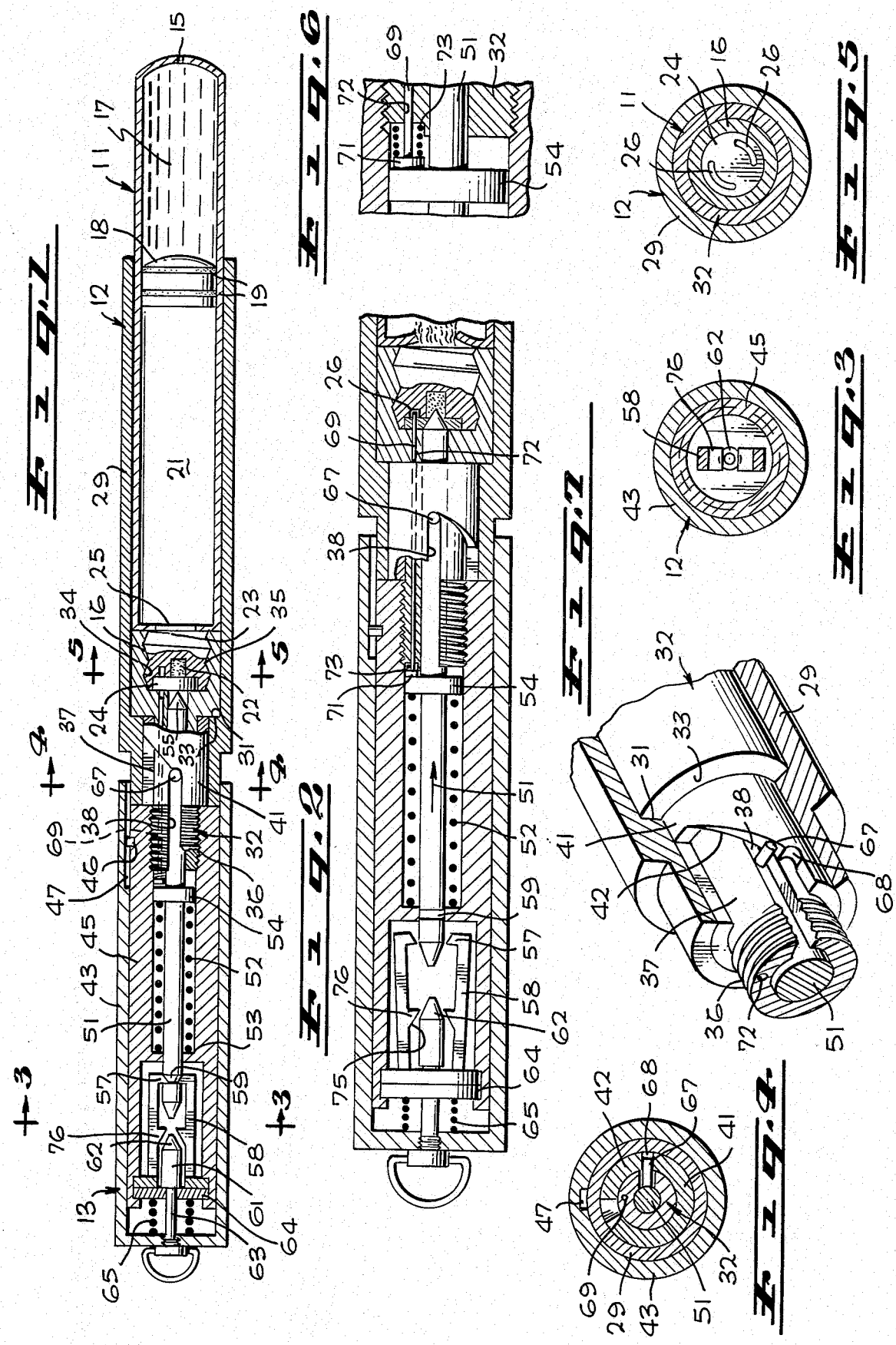

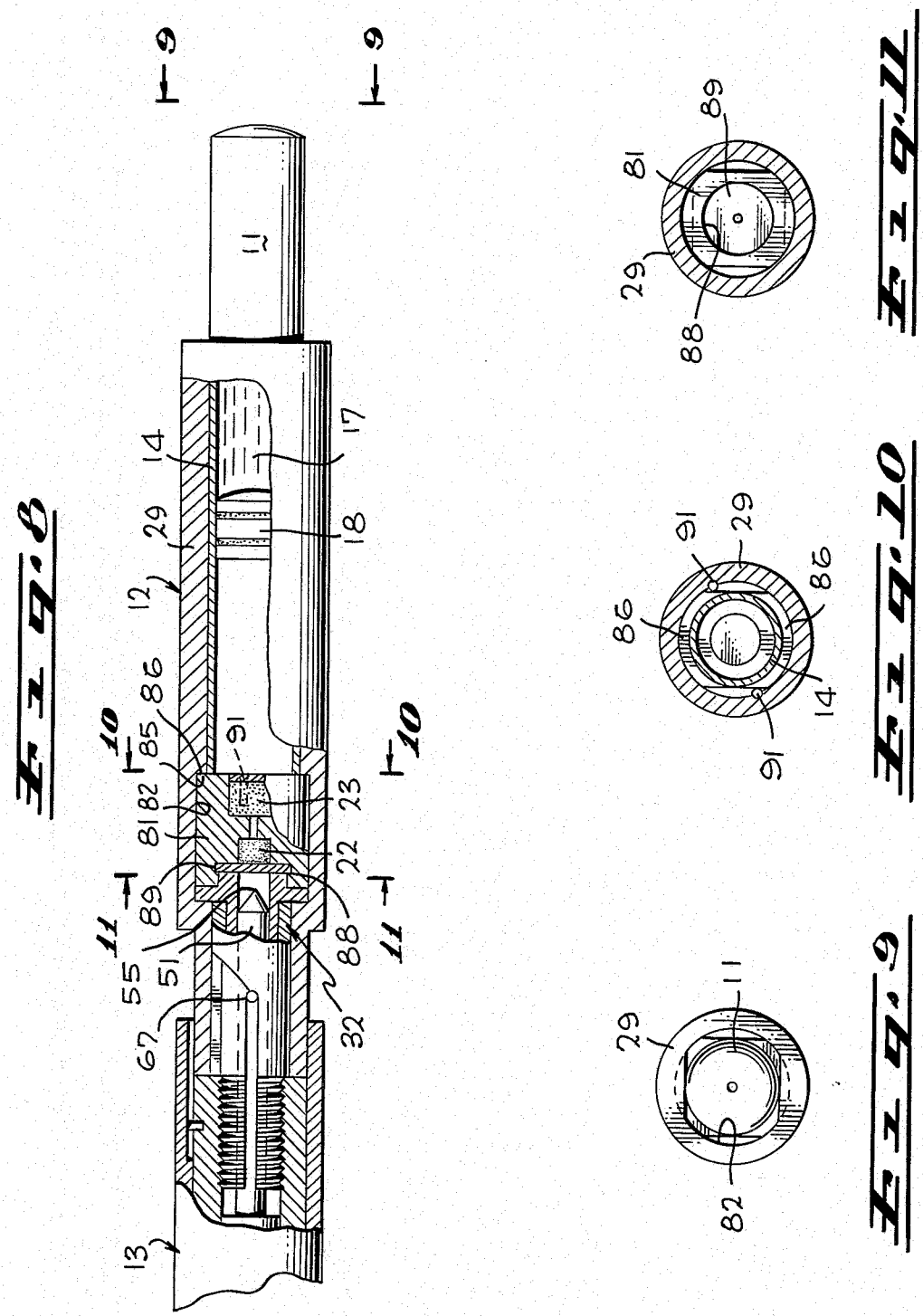

PYROTECHNICALLY POWERED NEEDLELESS INJECTOR

BACKGROUND OF THE INVENTION

1. Field of the Invention

This invention relates to needleless, gas operated piston-type injectors for introducing predetermined quantities of medicaments interstitially, and especially to such injectors in which a deflagatory pyrotechnic charge provides the fluid-injecting force. More particularly it relates to devices of this type wherein the powering charge, piston and medicament are contained within a disposable ampul.

2. Prior Art

The use of high pressure gas-propelled injectors in lieu of the common hypodermic syringe and needle for subcutaneous injection of fluid medicaments such as vitamins, vaccines, anaesthetics, and the like is well established. A number of typical prior art devices employing this technique are referred to and discussed in U.S. Pat. No. 3,802,430 (Schwebel and Arnold), which teaches the use of a single-shot preloaded pyrotechnic charge or deflagrant to propel a piston-actuated high velocity fluid injection system. In that patented apparatus, as in a number of the other prior art examples of gas operated injectors, both the triggering and actuating mechanisms and the gas-producing means are housed together. With this arrangement once the gas supply is exhausted the entire relatively costly unit, including the triggering and firing mechanisms, is of no further use and must be discarded.

In some instances this problem is obviated by providing for replacement or replenishment of the gas source; however, the structural requirements of this approach tend to make such devices overly complex and expensive to construct and maintain.

The object of the present invention is to provide a needleless, gas operated piston-type injector of sturdy, durable and relatively simple construction which avoids these and other deficiencies associated with the prior art gas operated injectors.

SUMMARY OF THE INVENTION

To achieve its stated objective, and other objects which will become apparent, the subject invention combines the deflagatory gas-producing charge, the gas operated piston and the pre-measured medicament in a unitary disposable ampul and incorporates the triggering and firing mechanisms in a reusable actuating unit. When the relatively slow burning deflagatory pyrotechnic charge is detonated, the gases produced drive the piston to eject the medicament through one or more orifices in the end of the ampul.

The injector includes a barrel formed to receive the ampul. The barrel is rotatably and slidably mounted to the housing carrying the triggering and firing mechanisms. The firing mechanism is armed by relative motion of the barrel and housing. The triggering mechanism activates the firing mechanism to detonate the charge within the ampul.

Since the piston is positioned between the propulsive charge and the medicament there is little likelihood of contamination or of injection of the gas under the skin. Sealing means are employed to preclude the possiblity of such contamination or injection.

The design and construction of the triggering and firing mechanisms and of the ampul and its receiver in the actuating unit provide positive protection against both accidental discharge and misfiring.

The structure and operation of the invention will become apparent to the reader upon consideration of the following detailed description of several of its preferred embodiments as illustrated in the accompanying drawing in which:

THE DRAWING

FIG. 1 is a side sectional view of a preferred embodiment of the invention prior to discharge, showing the firing mechanism cocked and safetied;

FIG. 2 is an enlarged fragmentary side sectional view of the embodiment of FIG. 1 immediately after detonation;

FIG. 3 is a cross-sectional view of the embodiment of FIG. 1, taken in the direction 3—3;

FIG. 4 is a cross-sectional view of the embodiment of FIG. 1, taken in the direction 4—4;

FIG. 5 is a cross-sectional view of the embodiment of FIG. 1, taken in the direction 5—5;

FIG. 6 is a fragmentary side sectional view of the embodiment of FIG. 1, further enlarged to show the ampul safety pin in its safe position;

FIG. 7 is an enlarged fragmentary perspective view of the embodiment of FIG. 1, with portions cut away to expose the firing plunger caming mechanism;

FIG. 8 is a side elevational view of another preferred embodiment of the invention, with portions cut away to expose the internal construction;

FIG. 9 is an end view of the embodiment of FIG. 8, taken in the direction 9—9;

FIG. 10 is a cross-sectional view of the embodiment of FIG. 8, taken in the direction 10—10; and FIG. 11 is a cross-sectional view of the embodiment of FIG. 8, taken in the direction 11—11.

Wherever practicable a single numeral is used for the same or functionally similar features in the several figures.

DETAILED DESCRIPTION

Referring to FIG. 1, a preferred embodiment of the invention comprises an ampul 11, an ampul receiver 12, and a unit 13 housing the triggering and firing mechanisms.

The ampul 11 (shown here in somewhat fanciful form for illustrative purposes only) consists of an elongated body having a relatively thin wall of glass, plastic, metal or other suitable material, having one or more orifices 15 at one end and an extended head 16 at its other end. A measured quantity of selected medicament 17 occupies the forward portion of the ampul 11. A reciprocal piston 18 is positioned between the head 16 and the region containing medicament 17. Conventional O-rings or seals 19 form a gas-tight seal between the chamber 21 defined by the piston 18 and the medicament 17.

The head 16 contains an explosive primer or percussion cap 22 operatively connected to the deflagatory charge 23 whose composition, quantity, form and other characteristics are carefully chosen so that on detonation the gaseous products introduced into chamber 21 impart to piston 18 the precise impulse necessary to eject the medicament 17 through orifice 15 under sufficient pressure to insure its subcutaneous infusion. A closure 24 and retainer 25 of suitable materials are provided to protect primer 22 and charge 23, respectively.

As shown more clearly in FIG. 5, a pair of arcuate recesses 26 are formed in the closure 24 in the underlying face of the head 16. The purpose of these recesses 26 will be explained later.

Receiver 12 comprises an elongated barrel 29 having an annular shoulder 31 formed on its inner wall. A bushing 32 sized to fit snugly but rotate freely within barrel 29 is formed with an annular shoulder 33 which abuts shoulder 31. One end of bushing 32 is provided with internal threads 34 of a relatively course pitch. The head 16 of ampul 11 is provided with external threads 35 of like pitch. The opposite end of bushing 32 is of reduced diameter and carries external threads 36. The portion of bushing 32 between shoulder 33 and the external threads 36 presents a smooth cylindrical bearing surface 37. An axial slot 38 is formed in the wall of bushing 32.

A sleeve 41 is secured to the inner wall of barrel 29 by brazing, soldering, welding or other conventional means. Sleeve 41 is sized to permit bushing 32 to rotate freely.

As best seen in FIGS. 4 and 7, a portion of the wall of sleeve 41 is cut away to provide a generally helical caming surface 42 extending about a quarter of the sleeve's circumference.

The trigger and firing mechanism unit 13 is housed in a casing 43 slidingly mounted on a sleeve 45 which is internally threaded at one of its ends for secure attachment to the threads 37 on the end of bushing 32. A slide pin 46 attached to the sleeve 45 and having its head extending into axial slot 47 permits casing 43 to move axially, but not to rotate, on sleeve 45.

An elongated firing pin 51 is mounted for axial movement within sleeve 45. A powerful compression spring 52 acting between an annular shoulder 53 formed on the inner wall of sleeve 45 and an annular boss 54 formed on firing pin 51 urges the chip 55 of firing pin 51 in the direction of primer 22. A pair of palls 57 at the ends of a pair of resilient, inwardly biased jaws 58 secured to the inner wall of sleeve 45 near its rear end fit into an annular groove 59 near the read end of firing pin 51 and restrain it against the thrust of spring 52.

A pin 61 having a frusto conical tip 62 is mounted axially at the read end of sleeve 45 with its elongated shank 63 extending slidably through a retainer washer 64 secured to the end of sleeve 45. The end of shank 63 is securely fastened to the closed rear end of casing 43. A compression spring 65 acting between the end of casing 43 and retainer washer 64 urges casing 43 in the direction away from receiver 12.

A cam pin 67 extends radially outwardly from firing pin 51, passes through slot 38 in bushing 32, and rides on the surface of the cam 42 formed in sleeve 41. It will be observed that by grasping the receiver 12 in one hand and the casing 43 in the other and twisting the former through about 90° with respect to the latter, cam pin 67 may be made to following cam 42, thereby forcing the firing pin 51 into the position shown in FIG. 1, where pawls 57 restrain it against the force exerted by compressed spring 52.

Preferably cam 42 is formed with a detent 68 at its end, which is adapted to retain cam pin 67, thereby preventing the accidental or inadvertant release of firing pin 51.

As seen most clearly in FIG. 6, an elongated safety pin 69 having an enlarged hed 71 extends through an axial bore 72 in bushing 32. A compression spring 73 acting between the head 71 of pin 69 and the end of bushing 32 maintains the head 71 in contact with the annular boss 54 on firing pin 51.

FIGS. 2 and 3 illustrate the operation of the triggering and firing mechanism of the embodiment shown in FIG. 1. With the ampul 11 securely threaded into the end of bushing 32, the firing mechanism is armed by rotating the receiver 12 and casing 43 as previously described until pawls 57 engage annular shoulder 53 and retain firing pin 51 in the position shown in FIG. 1. When the injection is to be given, the injector is armed by rotating receiver 12 and casing 43 in the opposite direction, thereby releasing cam pin 67 from detent 68 and returning the cam 42 to the position shown in FIGS. 2 and 3.

Grasping casing 43, the user places the tip of ampul 11 against the skin of the person to be injected. By applying sufficient force to overcome spring 65, casing 43 is moved axially in the direction of the receiver 12, thereby bringing the tip 62 of pin 61 into contact with the caming faces 75 of the pair of ears 76 formed on the inner faces of jaws 58 as pin 61 advances further, the caming action of tip 62 forces the resilient jaws 58 apart until pawls 57 are disengaged from annular groove 59, thereby releasing firing pin 51. Under the influence of spring 52 the tip 55 of firing pin 51 is driven through closure 24 and into primer 22 with sufficient force to ignite the primer, thereby detonating charge 23. The gases generated by the slow burning charge burst through retainer 25, fill and build up pressure within chamber 21, and drive piston 18 toward the tip of ampul 11, discharging the medicament 17 through orifice 15 with sufficient velocity to penetrate the skin and infuse the subcutaneous layer.

It will be noted that at the end of firing stroke, annular boss 54 on firing pin 51 has driven the end of safety pin 69 into the recess 26 aligned with bore 72. With the pin 69 in this position, ampul 11 cannot be rotated for release from bushing 32. To release ampul 11, it is necessary to rotate the receiver 12 and casing 43 to return the firing pin 51 to the cocked position of FIG. 1. This in turn permits compression spring 73 to draw the pin 69 out of recess 26, thereby freeing ampul 11 for rotation, disengagement from bushing 32, and removal from receiver 12. While not critical to the invention, this preferred feature serves as an automatic reminder to the user both to replace the spent ampul 11 and to arm the firing mechanism before each injection.

Referring now to FIGS. 8, 9, 10 and 11, the embodiment shown here comprises an ampul 11 containing a medicament 17, a gas operated piston 18, a primer 22 and deflagrant 23, a receiver 12 including a barrel 29 mounted for axial and rotary motion to a unit 13 housing triggering and firing mechanisms. This embodiment differs from the previous one principally in the means employed to secure the ampul 11 within the receiver 12.

In this embodiment, instead of the threaded, radially symmetrical head 16 previously described, the ampul 11 here has a head 81 of roughly rectangular cross-section. Likewise the inner walls 82 of the barrel 29 are of the same generally rectangular cross-section, being of greater extent along a first radial axis then along a second at right angles to it. The inner walls of the rear portion of this receiver 12 define a generally cylindrical chamber dimensioned to receive the head 81 of the ampul 11 but, by virtue of the "flatened" configuration of the mouth and throat of the receiver 12, having a pair of shoulders 85 extending radially outwardly of the inner walls 82 in the direction of the shorter cross-sectional axis of the mouth and throat of the receiver 12.

To insert this ampul 11, its head 81 is rotated until its major axis is aligned with the major axis of the mouth and throat of the receiver 82. When fully inserted into receiver 12, the ampul 11 is then rotated 90° to bring the shoulders 86 extending outwardly of the ampul walls 14 in the direction of the greater axis of head 81 into contact with the shoulders 85 of the chamber at the rear of receiver 12. This "key" arrangement serves to lock the ampul 11 tightly in place in receiver 12.

In this embodiment a recess 88 is formed in the rear of the head 81 and a spacer 89 is positioned within it. When the injector in this form has been fired, the spent ampul 11 can be removed, but as long as the firing pin 51 remains in its uncocked position, the spacer 89 comes in contact with the tip 55 of the firing pin 51 and prevents a new ampul 11 from being fully inserted into the receiver 12. This arrangement serves the same purpose as the safety pin 69 of the previous embodiment, that is, to remind the user to arm the trigger and firing mechanism to make the injector ready for use.

Preferably, a pair of stop pins 91 are positioned extending axially rearwardly into the chamber at the rear of the receiver 12 to insure alignment of shoulders 86 with shoulders 85.

Naturally, in this embodiment of the invention there is no need for the safety pin 69, compression spring 73 or bore 72. In all other respects the two embodiments are substantially identical.

With the foregoing in mind, what we claim as our invention is:

1. A pyrotechnically powered needleless injector for introducing a predetermined quantity of medicament interstitially through the skin, comprising:
    an elongated disposable ampul containing a quantity of a selected medicament and having an orifice at one end, a deflagatory gas-generating pyrotechnic charge at its other end, and a gas-operated piston positioned between said charge and said medicament to eject said medicament through said orifice under high pressure upon detonation of said charge;
    an elongated barrel open at one end to receive said ampul and having ampul-engaging means therein releasably securing said ampul in said barrel with the end of said ampul containing said charge being remote from the open end thereof;
    a first sleeve secured to the end of said barrel remote from the open end of said barrel;
    an elongated housing slidably mounted to said first sleeve for axial motion thereon;
    motion-limiting means preventing said housing from rotating about said first sleeve;
    firing pin means supported in said first sleeve for axial movement of one end thereof into charge-detonating contact with said ampul;
    first resilient means operatively mounted between said first sleeve and said firing pin, urging said firing pin toward said charge;
    a second sleeve secured to said barrel and having a cam formed thereon;
    a cam follower secured to said firing pin and positioned to ride said cam;
    retaining means effectively preventing said firing pin from rotating within said first sleeve, whereby rotation of said barrel in a first direction with respected to said housing moves said firing pin from a rest position to a cocked position more distant from said charge, wherein said first resilient means is compressed;
    restraining means mounted to said first sleeve engaging and releasably securing said firing pin in said cocked position; and
    triggering means mounted to said housing disengaging said restraining means from said firing pin in response to axial movement of said housing with respect to said barrel.

2. The injector of claim 1 comprising a detent formed in said cam releasably restraining said barrel against rotation in the direction opposite said first direction.

3. The injector of claim 1 wherein said retaining means comprises an axial slot formed in said barrel, said cam follower on said firing pin extending through, and being retained by the sides of said slot.

4. The injector of claim 3 comprising:
    an annular groove in said firing pin adjacent the opposite end;
    a pair of resilient arms mounted to said first sleeve and having a pair of opposed spaced ears extending radially inwardly thereof defining a space therebetween;
    a pair of pawls formed on said arms and releasably engaging said groove;
    a pin of a thickness greater than the space between said ears mounted to said housing and extending between said arms, means whereby said pin engages said ears and thereby spreads said arms to disengage said pawls from said groove in response to axial movement of said housing with respect to said barrel; and
    second resilient means operatively mounted between said housing and said first sleeve urging said pin out of engagement with said ears.

5. A pyrotechnically powered needleless injector for introducing a predetermined quantity of medicament interstitially through skin, comprising:
    a housing;
    an elongated disposable ampul containing a quantity of a selected medicament and having an orifice at one end, a deflagatory gas-generating pyrotechnic charge at its other end, and a gas-operated piston positioned between said charge and said medicament to eject said medicament through said orifice under high pressure upon detonation of said charge;
    an elongated barrel having a first portion slidably mounted within said housing and a second portion mounted to said first portion for rotational and axial motion relative thereto, means for receiving and releasably retaining said ampul in said second portion with the end of said ampul containing said charge adjacent said first portion;
    firing pin means axially and slidably supported in said first portion having one end extending into said second portion and adapted for axial movement within said barrel;
    resilient means operatively connected between said first portion and said firing pin, urging said firing pin into charge-detonating contact with the adjacent end of said ampul;
    a cam formed in said second portion adjacent said first portion and rotated by said second portion with respect to said housing;
    a cam follower on said firing pin riding said cam;

means for preventing said housing from rotating about said first portion;

retaining means secured to said first portion effectively retaining said firing pin against rotation relative to said first portion, whereby rotation of said second portion and cam with respect to said housing moves said firing pin in the direction away from said ampul into a predetermined cocked position, spaced from said ampul;

restraining means mounted to said first portion releasably engaging said firing pin in said cocked position and restraining said firing pin against the urging of said resilient means; and triggering means operatively positioned between said restraining means and said housing for disengaging said restraining means and said firing pin in response to axial movement of said barrel relative to said housing.

6. The injector of claim 5 comprising:

an annular groove in said firing pin adjacent the opposite end;

said restraining means including a resilient arm mounted to said first portion and including a pawl on said arm releasably engaging said groove in said firing pin;

caming means mounted to said housing and said resilient arm and positioned to engage said arm and force said pawl out of said groove in response to axial motion of said barrel with respect to said housing.

7. The injector of claim 5 comprising:

an annular groove in said firing pin adjacent the opposite end;

a pair of resilient arms mounted to said first portion and having a pair of opposed, spaced ears extending radially inwardly thereof defining a space therebetween;

a pair of pawls formed on said arms releasably engaging said groove; and a pin of thickness greater than said space between said ears mounted to said housing and extending between said arms, and means whereby said pin engages said ears and thereby disengages said pawls from said groove in response to axial motion of said barrel with respect to said housing.

8. The injector of claim 7 comprising second resilient means operatively connected between said first portion and said housing urging said pin out of engagement with said ears.

* * * * *